(12) United States Patent
Patel et al.

(10) Patent No.: US 12,005,137 B2
(45) Date of Patent: Jun. 11, 2024

(54) COSMETIC COMPOSITION

(71) Applicant: L'ORÉAL, Paris (FR)

(72) Inventors: Sonal Patel, Iselin, NJ (US); Balanda Atis, Green Brook, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/975,892

(22) Filed: Oct. 28, 2022

(65) Prior Publication Data
US 2024/0156712 A1 May 16, 2024

(51) Int. Cl.
*A61K 8/891* (2006.01)
*A61K 8/06* (2006.01)
*A61K 8/81* (2006.01)
*A61Q 17/04* (2006.01)

(52) U.S. Cl.
CPC .............. *A61K 8/891* (2013.01); *A61K 8/064* (2013.01); *A61K 8/8176* (2013.01); *A61Q 17/04* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 5,750,723 A | 5/1998 | Eldin et al. | |
| 6,048,918 A | 4/2000 | Eldin | |
| 8,637,057 B2 | 1/2014 | Patel et al. | |
| 2004/0234478 A1 | 11/2004 | Clapp et al. | |
| 2004/0247540 A1* | 12/2004 | Schulz | A61K 8/4946 424/59 |
| 2017/0231896 A1 | 8/2017 | Pascal et al. | |
| 2020/0368139 A1 | 11/2020 | Josephson et al. | |

FOREIGN PATENT DOCUMENTS

| | | |
|---|---|---|
| DE | 102011078092 A1 | 12/2012 |
| EP | 542669 A1 | 5/1993 |
| EP | 787730 A1 | 8/1997 |
| EP | 787731 A2 | 8/1997 |
| FR | 2931673 A | 12/2009 |
| WO | 96/08537 A | 3/1996 |
| WO | 2017141919 A1 | 12/2018 |

OTHER PUBLICATIONS

French Search Report, and Written Opinion, for corresponding French Application No. 2213961, dated Dec. 20, 2022.
Anonymous, "Time Shield Cushion Pact SPF 50+ PA+++", Database GNPD [Online] Mintel, XP93060727, Database accession No. 6289255, Jan. 23, 2019.
Anonymous, "Cushion SPF 50+ PA++++", Database GNPD [Online] Mintel, XP093060660, Database accession No. 8728951, May 24, 2021.

* cited by examiner

*Primary Examiner* — Nannette Holloman
(74) *Attorney, Agent, or Firm* — MEAGHER EMANUEL LAKS GOLDBERG & LIAO, LLP

(57) ABSTRACT

Disclosed is a leave-on water-in-oil cosmetic emulsion that includes an aqueous phase comprising water and a hydrophilic thickening agent consisting of polyvinylpyrrolidone, the aqueous phase being free of other hydrophilic thickening agents, a mattifying filler including a silicone elastomer, an organic ultraviolet filter consisting of octyl salicylate, at least one silicone oil, and at least one silicone emulsifier.

14 Claims, No Drawings

COSMETIC COMPOSITION

TECHNICAL FIELD

The present disclosure is drawn to cosmetic compositions, and particularly water-in-oil emulsions that provide ultraviolet (UV) protection.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Ultraviolet (UV) protection is desirable in a cosmetic product. However, most UV agents (such as octocrylene, homosalate, etc.) tend to make compositions feel oily. Adding various cosmetic ingredients, such as an oil-absorbing agent, can improve the feel, but using such materials tends to negatively impacts stability and reduce the UV protection factor. Thus, providing a cosmetic composition that is stable, provides a reasonable level of UV protection (e.g., SPF of 20), and has desirable aesthetic qualities can be challenging.

BRIEF SUMMARY

Various deficiencies in the prior art are addressed below by the disclosed systems, certain compositions may be provided. In some embodiments, a cosmetic emulsion may be provided. The cosmetic emulsion is preferably a leave-on product, and more preferably a leave-on water-in-oil cosmetic emulsion.

The cosmetic composition may include an aqueous phase comprising water and a hydrophilic thickening agent. The hydrophilic thickening agent may be polyvinylpyrrolidone (PVP), and the aqueous phase should be free of other hydrophilic thickening agents. The cosmetic composition may include a mattifying filler. The mattifying filler may include a silicone elastomer. The silicone elastomer may be, e.g., a non-glycerylated silicone. The mattifying filler may include a silicone elastomer, and may be free of other mattifying fillers. The cosmetic composition may include an organic ultraviolet filter consisting of octyl salicylate. The cosmetic composition may be free, or substantially free, of other ultraviolet filters. The cosmetic composition may include at least one silicone oil, and may include 40-60% by weight of the composition of the silicone oil(s). The cosmetic composition may include at least one silicone emulsifier. Optionally, the cosmetic composition may include an inorganic UV filter, which is preferably UV-grade titanium dioxide.

In some embodiments, the cosmetic composition may include no more than 10% by weight of the composition of hydrocarbon-based oil(s). In some embodiments, the cosmetic emulsion may be free of silica silylate. In some embodiments, the cosmetic composition may include 10% by weight or less of a polyol. In some embodiments, the cosmetic composition may include a colorant in an amount of 5-15% by weight of the composition. In some embodiments, the composition may include a preservative. In some embodiments, the composition may include a lipophilic thickening agent. In some embodiments, the composition may be substantially free of organic emulsifiers. In some embodiments, the composition may be substantially free of all other materials (e.g., materials other than the water, thickening agent, mattifying filler, organic UV filter, silicone emulsifier, silicone oil, hydrocarbon-based oil, polyol, colorant, preservative, and lipophilic thickening agent).

DETAILED DESCRIPTION

The following description merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others.

The term "substantially free of (a component)" as defined herein means that the systems or compositions contain no appreciable amount of the component, for example, no more than about 1% by weight, or no more than about 0.5% by weight, or no more than about 0.3% by weight, such as no more than about 0.1% by weight, based on the weight of the system or composition comprising the system and/or the oxidizing composition according to embodiments of the disclosure.

The term "free" or "completely free of (a component)" as defined herein means that the systems or compositions do not contain the component in any measurable degree by standard means.

In some embodiments, a cosmetic emulsion may be provided. The cosmetic emulsion is preferably a leave-on product, and more preferably a leave-on water-in-oil cosmetic emulsion.

Aqueous Phase

The cosmetic composition may include an aqueous phase comprising water and a thickening agent.

Water should be present in an amount no more than 30% by weight of the composition. In some embodiments, water may be present in an amount no more than 25% by weight of the composition. In some embodiments, water may be present in an amount no more than 20% by weight of the composition. In some embodiments, water may be present in an amount no more than 15% by weight of the composition. In some embodiments, water may be present in an amount no more than 10% by weight of the composition. In some embodiments, water may be present in an amount of 5-15% by weight of the composition.

Surprisingly, it has been found that the disclosed compositions work with a particular thickening agent, and do not provide the required characteristics when different thickening agents are used. The thickening agent should be polyvinylpyrrolidone (PVP). The aqueous phase should be free of other thickening agents. The thickening agent should be present in an amount no more than 3% by weight of the composition. In some embodiments, the thickening agent may be present in an amount no more than 2% by weight of the composition. In some embodiments, the thickening agent may be present in an amount no more than 1% by weight of the composition. In some embodiments, the thickening agent may be present in an amount of 0.5-1% by weight of the composition.

Mattifying Filler

The cosmetic composition may include a mattifying filler. The mattifying filler may include a silicone elastomer. The silicone elastomer may be, e.g., a non-glycerylated silicone. The mattifying filler may include a silicone elastomer and may be free or substantially free of other thickening agents.

Silicone Elastomer.

The amount of silicone elastomer present in the compositions, if included, will typically be at least 2%, or at least 3%, or at least 4%, or at least 5% by weight of the composition. It will typically be at most 7%, or at most 8%, or at most 9%, or at most 10% by weight of the composition.

The silicone elastomer should be a mattifying silicone polymer. The silicone elastomer may be a non-emulsifying silicon elastomer. The term "non-emulsifying" as used herein refers to organopolysiloxane elastomers that do not contain hydrophilic chains, in particular polyoxyalkylene (especially polyoxyethylene or polyoxypropylene) or polyglyceryl units. Thus, according to some embodiments, the composition may comprise a silicone elastomer that is free of polyoxyalkylene units and polyglyceryl units.

Non-limiting of non-emulsifying elastomers are described in U.S. Pat. No. 8,637,057, the disclosure of which is hereby incorporated by reference in its entirety, as well as those sold under the names KSG-6, KSG-15, KSG-16, KSG-18, KSG-41, KSG-42, KSG-43 and KSG-44 by the company Shin-Etsu, DC 9040, DC 9041, DC 9509, DC 9505 and DC 9506, by the company Dow Corning, and SFE 839 by the company General Electric.

The silicone elastomers may be in the form of a gel or a powder.

In some embodiments, the silicone elastomer may be conveyed in the form of a gel formed from an elastomeric organopolysiloxane included in at least one hydrocarbon-based oil and/or one silicone oil. In these gels, the organopolysiloxane particles are often non-spherical particles. Not limiting examples of silicone elastomers useful in this invention are dimethicone crosspolymer gels (blends of dimethicone crosspolymers in solvents) having viscosity values from about 150 and to about 700 mm$^2$/s, from about 200 to about 650 mm$^2$/s and from about 300 to about 600 mm$^2$/s, including all ranges and subranges therebetween.

Non-limiting examples of silicone elastomeric gels include DC EL-8040 ID (INCI name: Isododecane (and) Dimethicone Crosspolymer) and DC EL-9140 DM (INCI name: Dimethicone (and) Dimethicone Crosspolymer), supplied by Dow Corning.

Although not wishing to be bound by any particular theory, it is believed that the silicone elastomer thickens the composition, adds a cushiony (spongy) effect and/or improves the application properties of the composition. Also, it provides a very soft feel and mattifying effect after application.

In some embodiments, the cosmetic emulsion may be free or substantially free of other mattifying agents. In some embodiments, the cosmetic emulsion may be free of silica silylate. In some embodiments, the cosmetic emulsion may be free of an amorphous silica. In some embodiments, the cosmetic emulsion may be free of a starch.

Ultraviolet (UV) Filter

The cosmetic composition may include an ultraviolet filter. The ultraviolet filter may be an organic UV filter. The organic UV filter preferably consists of octyl salicylate. The cosmetic composition may be free, or substantially free, of other ultraviolet filters. The octyl salicylate maybe present in an amount no more than 5% by weight of the composition.

Silicone Oil

The cosmetic composition may include a silicone oil, which should be present in a total amount of at least 30% by weight of the composition. In some embodiments, the silicone oil may be present in a total amount of at least 35% by weight of the composition. In some embodiments, the silicone oil may be present in a total amount of at least 40% by weight of the composition. In some embodiments, the silicone oil may be present in a total amount of no more than 70% by weight of the composition. In some embodiments, the silicone oil may be present in a total amount of no more than 65% by weight of the composition. In some embodiments, the silicone oil may be present in a total amount of no more than 60% by weight of the composition. In some embodiments, the silicone oil(s) may be present in a total amount of 40-60% by weight of the composition. The cosmetic composition may include a single silicone oil, or may include a plurality of silicone oils. In some embodiments, the silicone oil may consist of dimethicone.

Volatile Silicone Oil.

In some embodiments, the silicone oil may include a volatile silicone oil. The term "volatile" oil refers to an oil that has a non-zero vapor pressure, at ambient temperature and atmospheric pressure, ranging in particular from 0.13 Pa to 40,000 Pa, in particular ranging to 13,000 Pa, and more particularly ranging to 1,300 Pa.

The volatile silicone oil may be chosen from linear or cyclic silicone oils such as linear or cyclic polydimethylsiloxanes (PDMS) having 3 to 7 silicon atoms. By way of example of such oils, mention may be made of octyltrimethicone, hexyltrimethicone, decamethylcyclopentasiloxane (cyclopentasiloxane or D5), octamethylcyclotetrasiloxane (cyclotetradimethylsiloxane or D4), dodecamethylcyclohexasiloxane (D6), decamethyltetrasiloxane (L4), polydimethysiloxanes such as those sold under the reference DC 200 (1.5 cSt), DC 200 (5 cSt), DC 200 (3 cSt) by Dow Corning, of KF 96 A of Shin Etsu; alone or in mixtures.

Preferably, the silicone oil may be free or substantially free of volatile silcone oils.

Non-Volatile Silicone Oils.

In some embodiments, the silicone oil may include a non-volatile silicone oil. The term "Non-volatile" oil refers to an oil of which the vapor pressure at 25° C. and atmospheric pressure, is not zero and less than $10^{-3}$ mm of Hg (0.13 Pa). By way of example, the vapor pressure may be measured according to the static method or the method of effusion by isothermic thermogravimetry, according to vapor pressure (norm OECD 104).

Among the non-volatile silicone oils that can be used in this invention, mention can be made for example of non-phenylated non-volatile silicone oils and phenylated non-volatile silicone oils.

The silicone oils that can be used in terms of the invention advantageously have a molecular weight less than or equal to 150,000 g/mol, preferably less than or equal to 100,000 g/mol, and better less than or equal to 10,000 g/mol.

Non-phenylated non-volatile silicone oils.

The expression "non-phenylated silicone oil" designates a silicone oil that does not comprise any phenyl substituents. Examples that are representative of these non-phenylated non-volatile silicone oils that can be mentioned, comprise polydimethylsiloxanes; alkyldimethicones; vinylmethylmethicones.

Note that these non-phenylated non-volatile silicone oils do not contain any patterns of the ethylene oxide, propylene oxide or glycerol type. They are therefore different from the silicone surfactants described hereinabove.

Moreover, the term "dimethicone" (INCI name) corresponds to a polydimethylsiloxane (chemical name).

In particular, these oils may be chosen from the following non-volatile oils: polydimethylsiloxanes (PDMS), alkyldimethicones comprising aliphatic groups, in particular alkyl, or alkoxy, which are pendant and/or at the end of the silicone chain; these groups each comprise from 2 to 24 carbon atoms. As an example mention can be made of cetyldimethicone sold under the trade name ABIL WAX 9801 from Evonik Goldschmidt, polydimethylsiloxanes comprising functional groups such as hydroxyl groups, substituted polydimethylsiloxane aliphatic groups, in particular $C_2$-$C_{24}$ alkyl, pendant and/or at the end of the silicone chain, and by functional groups such as hydroxyl groups, and mixtures thereof.

Preferably, these non-phenylated non-volatile silicone oils are chosen from polydimethylsiloxanes; alkyldimethicones and also from polydimethylsiloxanes substituted with aliphatic groups, in particular $C_2$-$C_{24}$ alkyl, and functional groups such as hydroxyl groups.

In a preferred embodiment, the silicone oil is only dimethicone.

The non-phenylated non-volatile silicone oil may be chosen from silicones having formula (I):

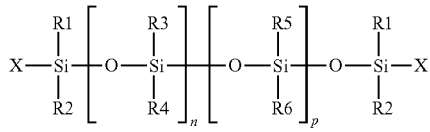

(I)

wherein:
$R_1$, $R_2$, $R_5$ and $R_6$ are, together or separately, an alkyl radical containing 1 to 6 carbon atoms,
$R_3$ and $R_4$ are, together or separately, an alkyl radical Containing 1 to 6 carbon atoms or a hydroxyl radical,
X is an alkyl radical containing 1 to 6 carbon atoms, a hydroxyl radical,
n and p are integers chosen in such a way as to have a fluid compound, in particular of which the viscosity at 25° C. is between 8 centistokes (cSt) (8×10−6 m²/s) and 800,000 cSt, advantageously less than 100,000 cSt, and advantageously a mean molar mass by weight less than or equal to 150,000 g/mol, preferably less than or equal to 100,000 g/mol, and better less than or equal to 10,000 g/mol.

Other non-volatile non-phenylated silicone oils that may be mentioned include those according to formula (I) where:
the substituents $R_1$ to $R_6$ and X represent a methyl group, and p and n are such that the viscosity is 60,000 cst, for example the product sold under the name Dow Corning 200 Fluid 60000 CS by Dow Corning, and the product sold under the name Wacker Belsil DM 60000 by Wacker,
the substituents $R_1$ to $R_6$ and X represent a methyl group, and p and n are such that the viscosity is 100 cSt, or 350 cSt, for example the products sold respectively under the names Belsil DM100, Dow Corning 200 Fluid 350 CS, by Dow Corning, and
the substituents $R_1$ to $R_6$ represent a methyl group, the group X represents a hydroxy group, and n and p are such that the viscosity is 700 cSt, for example the product sold under the name Baysilone Fluid T0.7 by Momentive.

Non-Volatile Phenylated Silicone Oils

The expression "phenylated silicone oil" designates a silicone oil that has at least one phenyl substituent. These non-volatile phenylated silicone oils may be chosen from those that furthermore have at least one dimethicone fragment, or from those that do not have any. Note that the terms "dimethicone fragment" designate a divalent siloxane group of which the silicon atom carried two methyl radicals, with this group not being located at the ends of the molecule. It can be represented by the following formula: $(Si(CH_3)_2O)$—.

The non-volatile phenylated silicone oil can as such be chosen from:
(A) phenylated silicone oils that have or do not have a dimethicone fragment corresponding to the following formula (II):

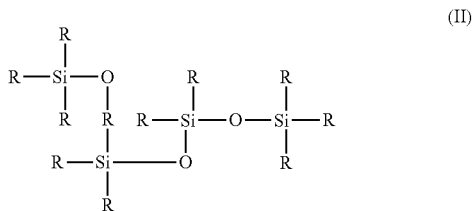

(II)

wherein the R groups, monovalent or divalent, are, independently from one another, a methyl, methylene, phenyl or phenylene, provided that at least one R group is a phenyl.

In some embodiments of formula (II), the phenylated silicone oil may include at least three phenyl groups, for example at least four, at least five or at least six.

(B) phenylated silicone oils that have or do not have a dimethicone fragment corresponding to the following formula (III):

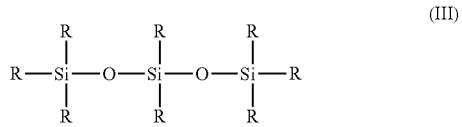

(III)

wherein the R groups are, independently from one another, a methyl or a phenyl, provided that at least one R group is a phenyl.

Preferably, in this formula, the compound of formula (III) comprises at least three phenyl groups, for example at least four or at least five.

Mixtures of the various phenylorganopolysiloxane compounds described hereinabove may be used.

Examples that can be mentioned comprise mixtures of triphenyl-, tetraphenyl-oru pentaphenyl-organopolysiloxanes.

Among the compounds having formula (III), more particularly mention can be made of phenylated silicone oils that do not have any dimethicone fragment corresponding to the formula (II) in which at least 4 or at least 5 R radicals are a phenyl radical with the remaining radicals being methyls.

Such non-volatile phenylated silicone oils are preferably trimethylpentaphenyl-trisiloxane, or tetramethyl-tetraphenyl-trisiloxane. They are in particular sold by Dow Corning under the reference PH-1555 HRI or Dow Corning 555 Cosmetic Fluid (chemical name: 1,3,5-trimethyl-1,1,3,5,5-pentaphenyl-trisiloxane; INCI name: trimethyl-pentaphenyltrisiloxane), or tetramethyl-tetraphenyl-trisiloxane sold under the reference Dow Corning 554 Cosmetic Fluid by Dow Corning can also be used.

They correspond in particular to the following formulas (III') and (III''):

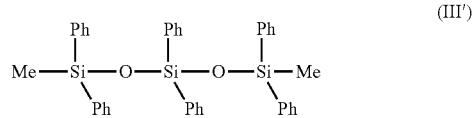

(III')

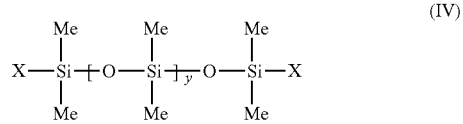

(III'')

wherein Me represents methyl, Ph represents phenyl.

(C) phenylated silicone oils that at least one dimethicone fragment corresponding to the following formula (IV):

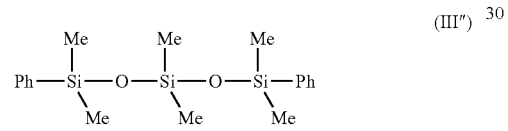

(IV)

wherein Me represents methyl, y is between 1 and 1,000 and X represents $CH_2CH(CH_3)(Ph)$.

(D) phenylated silicone oils corresponding to the formula (V) hereinbelow, and mixtures of the latter:

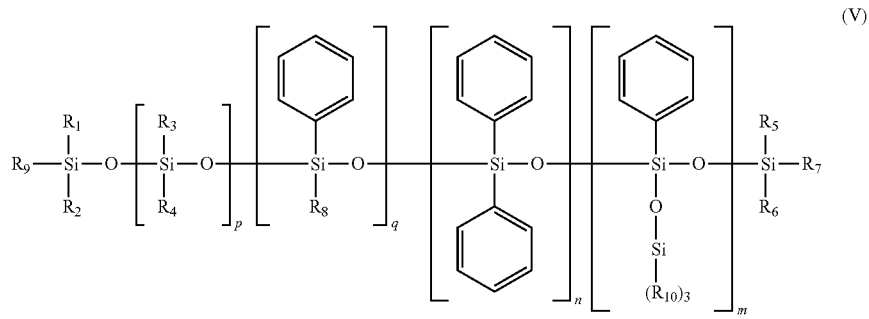

(V)

wherein:
$R_1$ to $R_{10}$, independently of each other, are $C_1$-$C_{30}$ linear, cyclic or branched, saturated or unsaturated hydrocarbon radicals, m, n, p and q are, independently of each other, integers between 0 and 900, provided that the sum m+n+q is different to 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of one other, are a $C_1$-$C_{30}$ linear or branched, saturated or unsaturated, preferably saturated, hydrocarbon radical, and in particular a $C_1$-$C_{20}$ hydrocarbon radical, preferably saturated, in particular $C_1$-$C_{18}$, or a $C_6$-$C_{14}$ aryl radical and in particular $C_{10}$-$C_{13}$, monocyclic or polycyclic, or an aralkyl radical preferably of which the alkyl portion is $C_1$-$C_3$.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical and, moreover, may be a methyl radical.

As particular embodiments of the formula (V), mention can be made of:
(1) phenylated silicone oils that have or do not have at least one dimethicone fragment corresponding to the formula (VI) hereinbelow, and mixtures of the latter:

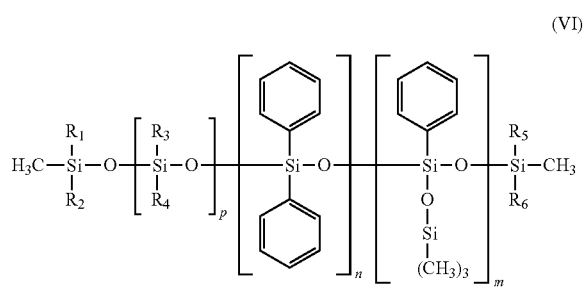

(VI)

wherein:
$R_1$ to $R_6$, independently of one other, are $C_1$-$C_{30}$ saturated or unsaturated, linear, cyclic or branched hydrocarbon radicals, an aryl radical, preferably $C_6$-$C_{14}$, or an aralkyl radical of which the alkyl portion is $C_1$-$C_3$).

m, n and p are, independently of one other, integers between 0 and 1000 and more preferably between 0 and 100, provided that the sum n+m is between 1 and 1000 and more preferably between 1 and 100.

Preferably, $R_1$ to $R_6$, independently of one other, are a hydrocarbon radical, preferably alkyl, $C_1$-$C_{20}$, in particular $C_1$-$C_{18}$, or a $C_6$-$C_{14}$ monocyclic aryl radical (preferably $C_6$) or polycyclic and in particular $C_{10}$-$C_{13}$, or an aralkyl radical (preferably the aryl portion is $C_6$; the alkyl portion is $C_1$-$C_3$).

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical and, moreover, may be a methyl radical. Preferably, m=1 or 2 or 3, and/or n=0 and/or p=0 or 1 can be applied, in formula (VI).

According to a particular embodiment, the non-volatile phenylated silicone oil is chosen from the phenylated silicone oils that have at least one dimethicone fragment.

Preferable, such oils correspond to compounds having the formula (VI) wherein:

m=0 and n and p are, independently of each other, integers between 1 and 100.

Preferably $R_1$ to $R_6$ are methyl radicals.

According to this embodiment, the silicone oil is preferably chosen from a diphenyldimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

p is between 1 and 1000, the sum n+m is between 1 and 1000, and n=0.

These phenylated silicone oils that have or do not have at least one dimethicone fragment corresponding more particularly to the formula (VII) hereinbelow:

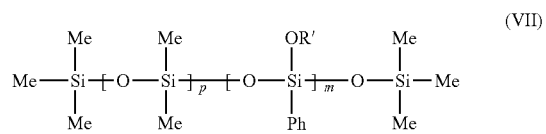

wherein Me is methyl and Ph is phenyl, OR' is a —OSiMe3 group and p is 0 or is between 1 and 1000, and m is between 1 and 1000. In particular, m and p are such that the compound (VII) is a non-volatile oil.

According to a first embodiment of non-volatile phenylated silicone that has at least one dimethicone fragment, p is between 1 and 1000. m is more particularly such that the compound (VII) is a non-volatile oil. For example, trimethylsiloxyphenyldimethicone can be used, sold in particular under the reference Belsil PDM 1000 by Wacker.

According to a second embodiment of non-volatile phenylated silicone that do not have any dimethicone fragment, p is equal to 0. m is between 1 and 1000, and in particular, is such that the compound (VII) is a non-volatile oil. For example, phenyltrimethicone can be used, sold in particular under the reference Dow Corning 556 Cosmetic Grade Fluid (DC556).

(E) phenylated non-volatile silicone oils that do not have any dimethicone fragment corresponding to the formula (VIII) hereinbelow, and mixtures of the latter:

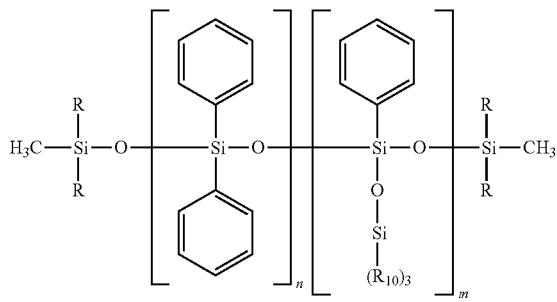

wherein:
R, independently of each other, are $C_1$-$C_{30}$ saturated or unsaturated, linear, cyclic or branched hydrocarbon radicals, preferably R is a $C_1$-$C_{30}$ alkyl radical, an aryl radical, preferably $C_6$-$C_{14}$, or an aralkyl radical of which the alkyl portion is $C_1$-$C_3$.

m and n are, independently of one other, integers between 0 and 100, provided that the sum n+m is between 1 and 100.

More preferably, R, independently of each other, are a $C_1$-$C_{30}$ saturated or unsaturated, linear or branched, preferably saturated, hydrocarbon radical, and in particular a hydrocarbon radical, preferably saturated, $C_1$-$C_{20}$, in particular $C_1$-$C_{18}$ and more particularly $C_4$-$C_{10}$, a $C_6$-$C_{14}$ monocyclic or polycyclic aryl radical and in particular $C_{10}$-$C_{13}$, or an aralkyl radical preferably the aryl portion is $C_6$ and the alkyl portion is $C_1$-$C_3$.

Preferably, Rs may each represent a methyl, ethyl, propyl, butyl, isopropyl, decyl, dodecyl or octadecyl radical, or alternatively a phenyl, tolyl, benzyl or phenethyl radical.

The Rs may in particular be identical and, moreover, may be a methyl radical.

Preferably, m=1 or 2 or 3, and/or n=0 and/or p=0 or 1 can be applied, in formula (VIII).

According to a preferred embodiment, n is an integer between 0 and 100 and m is an integer between 1 and 100, provided that the sum n+m is between 1 and 100, in the formula (VIII). Preferably, R is a methyl radical.

According to one embodiment, a phenylated silicone oil having formula (VIII) having a viscosity at 25° C. between 5 and 1500 mm2/s (i.e., from 5 to 1500 cSt), and preferably having a viscosity between 5 and 1000 mm2/s (i.e. 5 to 1000 cSt) can be used.

According to this embodiment, the non-volatile phenylated silicone oil is preferably chosen from phenyltrimethicones (when n=0) such as DC556 from Dow Corning (22.5 cSt), or from diphenylsiloxyphenyltrimethicone oil (when m and n are between 1 and 100) such as KF56 A from Shin Etsu, Silbione oil 70663V30 from Rhône-Poulenc (28 cSt). The values between brackets represent the viscosities at 25° C.

(F) phenylated silicone oils that have or do not have at least one dimethicone fragment corresponding to the following formula, and mixtures of the latter:

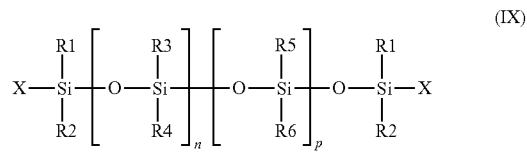

wherein:

R₁, R₂, R₅ and R₆ are, identical or not, an alkyl radical containing 1 to 6 carbon atoms, R₃ and R₄ are, identical or not, an alkyl radical containing 1 to 6 carbon atoms or an aryl radical (preferably $C_6$-$C_{14}$), with the condition that at least one of R₃ and R₄ is a phenyl radical, X is an alkyl radical containing 1 to 6 carbon atoms, a hydroxyl radical or a vinyl radical, n and p being an integer greater than or equal to 1, chosen in such w way as to confer to the oil a mean molar mass by weight preferably less than 150,000 g/mole and more preferably less than 100,000 g/mole.

and a mixture of the latter.

In accordance with a more suitable embodiment of the invention, the composition comprises at least one silicone oil, and preferably at least one non-volatile silicone oil.

Silicone Emulsifier

The cosmetic composition may include at least one silicone emulsifier. In some embodiments, the cosmetic composition may include at least two silicone emulsifiers.

The at least one silicone emulsifier should be present in a total amount of no more than 5% by weight of the composition. In some embodiments, the at least one silicone emulsifier should be present in a total amount of no more than 4% by weight of the composition. In some embodiments, the at least one silicone emulsifier should be present in a total amount of no less than 1% by weight of the composition. In some embodiments, the at least one silicone emulsifier should be present in a total amount of no less than 2% by weight of the composition.

Non-limiting examples of silicone emulsifiers include polyether substituted linear or branched polysiloxane copolymers. One preferred silicone emulsifier is PEG-10 dimethicone available under the tradename of ES-5612 from Dow Corning Corporation (Midland, Mich.), or KF-6017 from Shin-Etsu (Akron, Ohio). Another preferred silicone emulsifier is dimethicone (and) PEG/PPG-18/18 dimethicone available under the tradename of ES-5226 DM from Dow Corning Corporation (Midland, Mich.). Other suitable silicone emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

Hydrocarbon-Based Oil

In some embodiments, the cosmetic composition may include a hydrocarbon-based oil.

The term "hydrocarbon-based oil" is intended to mean an oil mainly comprising carbon and hydrogen atoms and optionally one or more functions chosen from hydroxyl, ester, ether and carboxylic functions. Generally, the oil has a viscosity of from 0.5 to 100 000 mPa s, preferably from 50 to 50 000 mPa s and more preferably from 100 to 300 000 mPa s.

In some embodiments, the hydrocarbon-based oil may include a volatile hydrocarbon-based oil. Non-limiting examples of a volatile hydrocarbon-based oils include hydrocarbon-based oils containing from 8 to 16 carbon atoms, and in particular $C_5$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_5$-$C_{16}$ esters and isohexyl neopentanoate, and mixtures thereof. Use may also be made of other volatile hydrocarbon-based oils, such as petroleum distillates, in particular those sold under the name Shell Solt by Shell; or volatile linear alkanes. Preferably, the composition may be free or substantially free of volatile hydrocarbon-based oils.

In some embodiments, the hydrocarbon-based oil may include a non-volatile hydrocarbon-based oil. Non-limiting examples of a non-volatile hydrocarbon-based oils include:

hydrocarbon-based oils of animal origin, such as perhydrosqualene;

linear or branched hydrocarbons of mineral or synthetic origin, such as liquid paraffins and their derivatives, petrolatum, polydecenes, polybutenes, hydrogenated polyisobutene, such as Parleam, or squalane;

phytostearyl esters, such as phytostearyl oleate, phytostearyl isostearate and lauroyl/octyldodecyl/phytostearyl glutamate (Ajinomoto, Eldew PS203®), triglycerides constituted of fatty acid esters of glycerol, in particular the fatty acids of which may have chain lengths ranging from $C_4$ to $C_{36}$, and in particular from $C_{18}$ to $C_{36}$, these oils possibly being linear or branched, and saturated or unsaturated; these oils may in particular be heptanoic or octanoic triglycerides, wheatgerm oil, sunflower oil, grapeseed oil, sesame seed oil (820.6 g/mol), corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passionflower oil or musk rose oil; shea oil; or alternatively caprylic/capric acid triglycerides, for instance those sold by the company Stearineries Dubois or those sold under the names Miglyol 810®, 812® and 818® by the company Dynamit Nobel;

synthetic ethers containing from 10 to 40 carbon atoms, such as dicaprylyl ether, hydrocarbon-based esters of formula RCOOR' in which RCOO represents a carboxylic acid residue comprising from 2 to 40 carbon atoms, and R' represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, diisopropyl adipate, heptanoates, and in particular isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethyl hexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

polyesters obtained by condensation of an unsaturated fatty acid dimer and/or trimer and of diol, such as those described in patent application FR 0 853 634, in particular such as dilinoleic acid and 1,4-butanediol. Mention may in particular be made in this respect of the polymer sold by Biosynthis under the name Viscoplast 14436H® (INCI name: Dilinoleic Acid/Butanediol Copolymer), or copolymers of polyols and of diacid dimers, and esters thereof, such as Hailuscent ISDA®, polyol esters and pentaerythritol esters, for instance dipentaerythritol tetrahydroxystearate/tetraisostearate, fatty alcohols containing from 12 to 26 carbon atoms, for instance octyldodecanol, 2-butyloctanol, 2-hexyldecanol, 2-undecylpentadecanol and oleyl alcohol, dialkyl carbonates, the two alkyl chains possibly being identical or different, such as dicaprylyl carbonate sold under the name Cetiol CC® by Cognis.

hydroxylated esters such as polyglyceryl-2 triisostearate, and aromatic esters such as tridecyl trimellitate, $C_{12}$-$C_{15}$ alcohol benzoate, the 2-phenylethyl ester of benzoic acid, and butyloctyl salicylate.

The hydrocarbon-based oil, when present, should be present in an amount no more than 20% by weight of the composition. In some embodiments, the hydrocarbon-based oil may be present in a total amount of no more than 15% by weight of the composition. In some embodiments, the hydrocarbon-based oil may be present in a total amount of no more than 10% by weight of the composition. In some embodiments, the hydrocarbon-based oil may be present in a total amount of no less than 1% by weight of the composition. In some embodiments, the hydrocarbon-based oil may be present in a total amount of no less than 2% by weight of the composition. In some embodiments, the hydrocarbon-based oil may be present in a total amount of no less than 3% by weight of the composition. In some embodiments, the hydrocarbon-based oil may be present in a total amount of no less than 4% by weight of the composition. In some embodiments, the hydrocarbon-based oil may be present in a total amount of no less than 5% by weight of the composition.

Polyol

In some embodiments, the cosmetic composition may include a polyol. In some embodiments, the polyol may be a hydrocarbon-based polyol. In some embodiments, the polyol may be present in a total amount no more than 15% by weight of the composition. In some embodiments, the polyol may be present in a total amount no more than 12% by weight of the composition. In some embodiments, the polyol may be present in a total amount no more than 5% by weight of the composition. In some embodiments, the polyol may be present in a total amount between 5% and 10% by weight.

In some embodiments, the composition may include a plurality of polyols present in a total amount greater than 1% by weight of the composition, and a plurality of polyols present in a total amount less than 0.5% by weight of the composition.

The term "polyol" should be understood as meaning any organic molecule comprising at least two free hydroxyl groups. Preferably, the polyol may be present in liquid form at room temperature.

In various embodiments, the polyol that is suitable for use in the invention may be a compound of linear, branched or cyclic, saturated or unsaturated alkyl type, bearing on each alkyl chain at least two OH functions, in particular at least three OH functions and more particularly at least four OH functions.

In some embodiments, the polyol may contain from 2 to 32 carbon atoms preferably 2 to 20 carbon atoms and more preferably 2 to 16 carbon atoms, advantageously 2 to 10 carbon atoms, more advantageously 2 to 6 carbon atoms.

In some embodiments, the polyol may be a polyethylene glycol.

In some embodiments, the polyol may be a polyhydric alcohol, preferably of $C_2$-$C_8$ and more preferably $C_3$-$C_6$. Non-limiting examples of such include glycerol, pentaerythritol, trimethylolpropane, ethylene glycol, propylene glycol, 1,3-butylene glycol, 1,3-propanediol, pentylene glycol, hexylene glycol, isoprene glycol, dipropylene glycol, diethylene glycol and diglycerol, ethylhexylglycerine, caprylyl glycol and mixtures thereof, glycerol and derivatives thereof, polyglycerols, such as glycerol oligomers, for instance diglycerol, and polyethylene glycols, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

In some embodiments, the polyol may include one polyol present in an amount of at least 5% by weight of the composition, and the polyol may be substantially free of other polyols.

Inorganic UV Filter

The inorganic UV filter may consist of UV-grade titanium dioxide, and the cosmetic composition may be free of other inorganic ultraviolet filters. "UV-grade" titanium dioxide generally has a relatively small particle size—typically having mean particle sizes of 250 nm or smaller, including 200 nm or smaller, and/or 150 nm or smaller. In some cases, the average particle size is around 130 nm.

The inorganic UV filter will typically be present in an amount less than 15% by weight of the composition. In some embodiments, the inorganic UV filter may be present in an amount less than 10% by weight of the composition. In some embodiments, the inorganic UV filter may be present in an amount less than 7% by weight of the composition. In some embodiments, the inorganic ultraviolet filter may be present in an amount less than 5% by weight of the composition. In some embodiments, the inorganic ultraviolet filter may be present in an amount less than 3% by weight of the composition. In some embodiments, the composition may be free, or substantially free, of the inorganic ultraviolet filter.

Colorant

The cosmetic composition may include a colorant. In some embodiments, the colorant may be present in an amount of less than 30% by weight of the composition. In some embodiments, the colorant may be present in an amount of less than 20% by weight of the composition. In some embodiments, the colorant may be present in an amount of less than 15% by weight of the composition. In some embodiments, the colorant may be present in an amount of at least 5% by weight of the composition. In some embodiments, the colorant may be present in an amount of at least 10% by weight of the composition. In some embodiments, the cosmetic composition may include a colorant in an amount of 5-15% by weight of the composition.

The colorant(s) may be selected from organic and/or inorganic colorants, in particular such as pigments or nacres conventionally used in cosmetic compositions, liposoluble or water-soluble coloring agents, materials with a specific optical effect, and mixtures thereof.

In some embodiments, the composition may include a single pigment between 5-10% by weight of the composition, a pearlescent pigment of at least 1% by weight of the composition, and may be substantially free of all other colorants.

Pigments.

The colorant may include, or consist of, one or more pigments. Each pigment is preferably coated. In some embodiments, the one or more pigments comprises pigment-grade titanium dioxide. "Pigment-grade" titanium dioxide generally has a larger particle size than UV grade titanium dioxide—typically having mean particle sizes of 400 nm or larger, including 500 nm or larger, and/or 600 nm or larger.

The term "pigments" should be understood to mean white or colored, inorganic or organic particles which are insoluble in an aqueous solution and are intended for coloring and/or opacifying the resulting film.

The pigments may be present in a proportion of from 0.1% to 30% by weight, such as from 1% to 30% by weight, or from 5% to 20% by weight, relative to the total weight of the cosmetic composition.

As inorganic pigments that can be used, mention may be made of titanium dioxide, zirconium oxide or cerium oxide, and also zinc oxide, iron oxide or chromium oxide, ferric blue, manganese violet, ultramarine blue and chromium hydrate.

The pigment may also be a pigment having a structure which may be, for example, of sericite/brown iron oxide/titanium dioxide/silica type. Such a pigment is sold, for example, under the reference Coverleaf NS or JS by the company Chemicals and Catalysts and has a contrast ratio of around 30.

The colorant may also comprise a pigment having a structure which may, for example, be of the type of silica microspheres containing iron oxide. An example of a pigment having this structure is sold by the company Miyoshi under the reference PC Ball PC-LL-100 P, this pigment being composed of silica microspheres containing yellow iron oxide.

Among the organic pigments that can be used, mention may be made of carbon black, D & C pigments, lakes based on cochineal carmine, on barium, strontium, calcium or aluminum, or else the diketopyrrolopyrroles (DPP) described in documents EP-A-542 669, EP-A-787 730, EP-A-787 731 and WO-A-96/08537.

In some embodiments, the coating may include alumina, silica, aluminum hydroxide, or pigment-grade titanium dioxide, and a hydrocarbon-based emulsifier as disclosed herein. In some embodiments, the coating may be present in a total amount of less than 1% by weight of the composition.

When iron oxides are present, such iron oxides (i.e., excluding coatings) are present in a total amount of no more than 5% by weight of the composition. In some embodiments, such iron oxides (excluding coatings) are present in a total amount of no more than 3% by weight of the composition. In some embodiments, such iron oxides (excluding coatings) are present in a total amount of no more than 2% by weight of the composition. In some embodiments, such iron oxides (excluding coatings) are present in a total amount of 1-1.5% by weight of the composition.

When pigment-grade titanium dioxide is present, such pigment-grade titanium dioxide (i.e., excluding coatings) is present in a total amount of no more than 20% by weight of the composition. In some embodiments, such pigment-grade titanium dioxide (excluding coatings) are present in a total amount of no more than 15% by weight of the composition. In some embodiments, such pigment-grade titanium dioxide (excluding coatings) is present in a total amount of 5-10% by weight of the composition.

Nacres.

The colorant may also include one or more nacres. The term "nacres" should be understood to mean iridescent or noniridescent colored particles of any shape, which are in particular produced by certain molluscs in their shell or else are synthesized, and which exhibit a color effect by optical interference.

The nacres may be selected from pearlescent pigments. Such pigments may include natural or synthetic mica (fluorphlogopite). Non-limiting examples of pearlescent pigments invention include white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. This may also involve mica particles at the surface of which are superposed at least two successive layers of metal oxides and/or of organic colorants. If pearlescent pigments are present, they are typically present in a total amount of no more than 5% by weight of the composition. In some embodiments, pearlescent pigments are present in a total amount of no more than 3% by weight of the composition. In some embodiments, pearlescent pigments are present in a total amount of no more than 2% by weight of the composition.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart and the synthetic-mica-based Sunshine nacres sold by the company Sun Chemical.

The nacres may more particularly possess a yellow, pink, red, bronze, orange, brown, gold and/or copper color or glint.

By way of illustration of nacres which can be used in the context of the present disclosure, mention may in particular be made of the golden nacres sold in particular by the company Engelhard under the name Brillant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown-hued nacres sold in particular by the company Engelhard under the name Nu-antique copper 340XB (Cloisonne) and Brown CL4509 (Chromalite); the copper-glint nacres sold in particular by the company Engelhard under the name Copper 340A (Timica); the red-glint nacres sold in particular by the company Merck under the name Sienna fine (17386) (Colorona); the yellow-glint nacres sold in particular by the company Engelhard under the name Yellow (4502) (Chromalite); the gold-glint red-hued nacres sold in particular by the company Engelhard under the name Sunstone G012 (Gemtone); the pink nacres sold in particular by the company Engelhard under the name Tan opale G005 (Gemtone); the gold-glint black nacres sold in particular by the company Engelhard under the name Nu antique bronze 240 AB (Timica), the blue nacres sold in particular by the company Merck under the name Matte blue (17433) (Microna), the silver-glint white nacres sold in particular by the company Merck under the name Xirona Silver and the green-gold and pinkish orangish nacres sold in particular by the company Merck under the name Indian summer (Xirona), and mixtures thereof.

Dyes.

The colorant may also include water-soluble or liposoluble dyes. The liposoluble dyes are, for example, Sudan red, DC Red 17, DC Green 6, β-carotene, soya oil, Sudan brown, DC Yellow 11, DC Violet 2, DC orange 5 and quinoline yellow. The water-soluble dyes are, for example, beetroot juice and caramel.

Material with a Special Optical Effect.

The colorant may also include at least one material with a specific optical effect. This effect is different than a simple, conventional hue effect, i.e., a unified and stabilized effect of the kind produced by conventional colorants, such as, for example, monochromatic pigments. For the purpose of the present disclosure, the term "stabilized" signifies absence of an effect of variability of color with the angle of observation or else in response to a temperature change. For example, this material may be selected from particles having a metallic glint, goniochromatic coloring agents, diffracting pigments, thermochromatic agents, optical brighteners, and also fibers, in particular of interference type. Of course, these various materials may be combined so as to provide the simultaneous manifestation of two effects, or even a new effect.

The metallic-glint particles that can be used in the present disclosure are in particular selected from: (i) particles of at least one metal and/or of at least one metal derivative; (ii) particles comprising a single-substance or multi-substance, organic or inorganic substrate, at least partially coated with at least one metal-glint layer comprising at least one metal and/or at least one metal derivative, and (iii) mixtures of such particles. The term "metal derivatives" denotes compounds derived from metals, in particular oxides, fluorides, chlorides and sulfides.

Non-limiting examples of metals that may be present in such particles include Ag, Au, Cu, Al, Ni, Sn, Mg, Cr, Mo, Ti, Zr, Pt, Va, Rb, W, Zn, Ge, Te, Se and mixtures or alloys thereof, such as Ag, Au, Cu, Al, Zn, Ni, Mo, Cr and mixtures or alloys thereof (for example, bronzes and brasses).

By way of illustration of these particles, mention may be made of aluminum particles, such as those sold under the names STARBRITE 1200 EAC® by the company Siberline and METALURE® by the company Eckart. Mention may also be made of metal powders of copper or of alloy mixtures, such as the references 2844 sold by the company Radium Bronze, metal pigments, such as aluminum or bronze, for instance those sold under the name Rotosafe 700 by the company Eckart, the silica-coated aluminum particles sold under the name Visionaire Bright Silver from the company Eckart, and the metal alloy particles such as silica-coated bronze (copper and zinc alloy) sold under the name Visionaire Bright Natural Gold from the company Eckart. The particles in question may also be particles comprising a glass substrate, such as those sold by the company Nippon Sheet Glass under the name Microglass Metashine.

The goniochromatic coloring agent may be selected, for example, from multilayer interference structures and liquid-crystal coloring agents.

Examples of symmetrical multilayer interference structures that may be used in compositions prepared in accordance with the present disclosure are, for example, the following structures: Al/SiO$_2$/Al/SiO2/Al, pigments having this structure being sold by the company Dupont de Nemours; Cr/MgF2/Al/MgF2/Cr, pigments having this structure being sold under the name Chromaflair by the company Flex; MoS2/SiO2/Al/SiO2/MoS2; Fe$_2$O$_3$/SiO2/Al/SiO2/Fe2O3 and Fe$_2$O$_3$/SiO2/Fe2O3/SiO2/Fe2O3, pigments having these structures being sold under the name Sicopearl by the company BASF; MoS2/SiO2/mica-oxide/SiO2/MoS2; Fe$_2$O$_3$/SiO2/mica-oxide/SiO2/Fe2O3; TiO2/SiO2/TiO2 and TiO2/Al$_2$O$_3$/TiO2; SnO/TiO2/SiO2/TiO2/SnO; Fe$_2$O$_3$/SiO2/Fe2O3; SnO/mica/TiO2/SiO2/TiO2/mica/SnO, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Carribean Blue sold by the company Merck. Mention may also be made of the Infinite Colors pigments from the company Shiseido. Depending on the thickness and the nature of the various layers, various effects are obtained. Thus, with the Fe$_2$O$_3$/SiO2/Al/SiO2/Fe2O3 structure, the color changes from green-golden to red-gray for SiO2 layers of 320 to 350 nm; from red to golden for SiO2 layers of 380 to 400 nm; from violet to green for SiO2 layers of 410 to 420 nm; from copper to red for SiO2 layers of 430 to 440 nm.

By way of example of pigments with a polymeric multilayer structure, mention may be made of those sold by the company 3M under the name Color Glitter.

Examples of liquid-crystal goniochromatic particles that may be used include those sold by the company Chenix, and also the product sold under the name HELICONE® HC by the company Wacker.

Preservative

In some embodiments, the composition may include a preservative. In some embodiments, the composition may include a plurality of preservatives. In some embodiments, the preservative may be present in an amount no more than 2% by weight of the composition.

Non-limiting examples of preservatives include phenoxyethanol, benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenesin, Triclosan, Chlorhexidine digluconate, Imidazolidinyl Urea, and Diazolidinyl Urea. Any or all may be used alone or in combination with each other.

Lipophilic Thickening Agent

In some embodiments, the composition may include a lipophilic thickening agent. The lipophilic thickening agent preferably consists of a modified clay. In some embodiments, the total amount of the lipophilic thickening agent is less than 3% by weight of the composition. In some embodiments, the total amount of the lipophilic thickening agent is less than 2% by weight of the composition. In some embodiments, the total amount of the lipophilic thickening agent is less than 1.5% by weight of the composition. In some embodiments, the total amount of the lipophilic thickening agent is at least 0.5% by weight of the composition. In some embodiments, the total amount of the lipophilic thickening agent is at least 1% by weight of the composition.

Clays are silicates containing a cation that may be chosen from calcium, magnesium, aluminium, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names LAPONITE XLS, LAPONITE XLG, LAPONITE RD, LAPONITE RDS and LAPONITE XL21 (these products are sodium magnesium silicates and in particular sodium lithium magnesium silicates); bentonites, such as the product sold under the name BENTONE HC by Rheox; magnesium aluminium silicates, which are in particular hydrated, such as the products sold by Vanderbilt Company under the name VEEGUM ULTRA, VEEGUM HS or VEEGUM DGT, or also calcium silicates and in particular that in synthetic form sold by the company under the name MICRO-CEL C.

In some instances organophilic clays are preferred, more particularly modified clays, such as montmorillonite, bentonite, hectorite, attapulgite and sepiolite, and mixtures thereof. The clay is preferably an optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name BENTONE 38V, BENTONE 38V CG or BENTONE EW CE by the company Elementis, or stearalkonium hectorites, such as BENTONE 27 V. In some instances, the clay is preferably disteardimonium hectorite.

Mention may also be made of quaternium-18 bentonites, such as those sold under the names BENTONE 34 by the company Elementis, TIXOGEL VP by the company United Catalyst and CLAYTONE 40 by the company Southern Clay; stearalkonium bentonites, such as those sold under the names TIXOGEL LG by the company United Catalyst and CLAYTONE AF and CLAYTONE APA by the company Southern Clay; or quaternium-18/benzalkonium bentonites, such as that sold under the name CLAYTONE HT by the company Southern Clay.

In some instances, it is preferable that the clay is chosen from organophilic modified clays, in particular organophilic modified hectorites, in particular modified with distearyldimethylammonium chloride (CTFA name: Disteardimonium hectorite).

In some embodiments, the total amount of the modified clays is less than 3% by weight of the composition. In some embodiments, the total amount of the modified clays is less than 2% by weight of the composition. In some embodiments, the total amount of the modified clays is less than 1.5% by weight of the composition. In some embodiments, the total amount of the modified clays is at least 0.5% by weight of the composition. In some embodiments, the total amount of the modified clays is at least 1% by weight of the composition.

Other Materials

In some embodiments, the composition may be free or substantially free of all other materials (e.g., materials other than the water, thickening agent, mattifying filler, organic UV filter, silicone emulsifier, silicone oil, hydrocarbon-based oil, polyol, colorant, preservative, and lipophilic thickening agent).

In some embodiments, the composition may include vitamins and/or extracts, pH adjusting or buffering agents, and pigment coatings.

In some embodiments, the composition may be substantially free of organic emulsifiers.

Vitamins and Extracts.

In some embodiments, the composition may include a vitamin. In some embodiments, the composition may include a plurality of vitamins. Such vitamins include materials having vitamin activity. In some embodiments, the vitamins may be present in a total amount no more than 0.5% by weight of the composition. In some embodiments, the vitamins may be present in a total amount no more than 0.3% by weight of the composition. In some embodiments, the vitamins may be present in a total amount no less than 0.1% by weight of the composition. In some embodiments, the vitamins may be present in a total amount no less than 0.2% by weight of the composition. In some embodiments, the vitamins may be present in a total amount of 0.15%-0.3% by weight of the composition.

Non-limiting examples of such vitamins include Vitamin K, Vitamin B8, Vitamin B12, Thiamine riboflavin, Nicotinamide (also referred to as Niacinamide), Pantothenic acid, Pyridoxine and derivatives, biotin (vitamin B7), folic acid, cyanocobalamin and Ascorbic acid. Vitamins include vitamin derivatives. For example, ascorbic acid (vitamin C) and derivatives thereof, especially the phosphate derivatives thereof such as the potassium salt of di-alpha-tocopheryl diascorbyl phosphate (sold by the company Senju Pharmaceutical under the reference Sepivital EPC), magnesium ascorbyl phosphate and sodium ascorbyl phosphate (sold by the company Roche under the reference Stay-C 50), and esters thereof such as ascorbyl acetate, palmitate and propionate; retinol (vitamin A) and derivatives thereof, especially esters thereof such as retinyl acetate, palmitate and propionate; as well as pantothenic acid (vitamin B) and derivatives thereof such as pantolactone, and D-panthenol.

In some embodiments, the composition may include an extract. In some embodiments, the composition may include a single extract. In some embodiments, the composition may include a plurality of extracts. In some embodiments, the extract may be present in a total amount no more than 0.5% by weight of the composition. In some embodiments, the vitamins may be present in a total amount no more than 0.1% by weight of the composition. In some embodiments, the vitamins may be present in a total amount no more than 0.01% by weight of the composition. In some embodiments, the vitamins may be present in a total amount no less than 0.001% by weight of the composition. Non-limiting examples of extracts include, e.g., plant extracts, in particular criste marine extracts, olive leaf extracts, *Lycium barbarum* fruit extract, as well as plant proteins and their hydrolysates such as rice or soybean protein hydrolysates; extracts from algae, in particular from laminaria; bacterial extracts; sapogenins such as diosgenin and extracts from Dioscoreae, in particular from wild yam.

pH Adjusting or Buffering Agent.

In some embodiments, the composition may include a pH adjusting and/or buffering agent.

pH adjusters include, but are not limited to, sodium metasilicate, silicate compounds, citric acid, lactic acid, ascorbic acid, and carbonate compounds, and sodium hydroxide.

Non-limiting examples of buffering agents include an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), or a Hepes buffer (4-(2-hydroxyethyl)-1-piperazineethanesulfonic acid).

In some embodiments, the thickening agent is present in an amount less than 3% by weight of the composition. In some embodiments, the composition is substantially free of both a pH adjuster and buffering agent. In some embodiments, the pH adjuster and buffering agent may be present in a total amount of 0.001-0.5% by weight of the composition.

Pigment Coatings.

In some embodiments, when the pigment is coated, various coatings may be used. In some embodiments, the coating of the pigments may comprise at least one compound selected from alumina, silica, and aluminum hydroxide. In some embodiments, the coating of the pigments may include an anionic surfactant. Non-limiting examples of which include acyl glutamates, for instance, disodium stearoyl glutamate and sodium stearoyl glutamate.

In some embodiments, the pigment coatings may be present in a total amount no more than 0.5% by weight of the composition. In some embodiments, the pigment coatings may be present in a total amount no more than 0.3% by weight of the composition. In some embodiments, the pigment coatings may be present in a total amount no less than 0.2% by weight of the composition. In some embodiments, the pigment coatings may be present in a total amount no less than 0.15% by weight of the composition. In some embodiments, the pigment coatings may be present in a total amount no less than 0.1% by weight of the composition. In some embodiments, the pigment coatings may be present in a total amount of 0.15%-0.3% by weight of the composition.

EXAMPLE

Compositions such as those shown in Table 1 below, can be created by first mixing the oils, oil-soluble ingredients in a container, mixing the water and water-soluble ingredients in a separate container, then while homogenizing, combining the two phases, and then adding the mattifying fillers and colorants.

TABLE 1

(Exemplary and Comparative Formulas)

| Material Name | Ex 1 | Ex 2 | C 1 | C 2 | C 3 |
|---|---|---|---|---|---|
| PVP | 0.7 | 0.2 | — | — | — |
| VP/Eicosene Copolymer | — | — | — | 1.0 | — |
| Acrylates Copolymer | — | — | — | — | 1.0 |
| Water | qs | qs | qs | qs | qs |
| Dimethicone Crosspolymer | 6.3 | 6.3 | 6.3 | 6.3 | 6.3 |
| Octyl Salicylate | 5.0 | 5.0 | 5.0 | 5.0 | 5.0 |
| PEG-10 Dimethicone | 1.1 | 1.1 | 1.1 | 1.1 | 1.1 |
| PEG-9 Polydimethylsiloxyethyl Dimethicone | 2.0 | 2.0 | 2.0 | 2.0 | 2.0 |
| Dimethicone | 48.7 | 48.7 | 48.7 | 48.7 | 48.7 |
| Pigment-Grade TiO2 | 7.0 | 7.0 | 7.0 | 7.0 | 7.0 |
| Pearlescent Pigment | 2.2 | 2.2 | 2.2 | 2.2 | 2.2 |
| Other Pigments | 0.7 | 0.7 | 0.7 | 0.7 | 0.7 |
| Pigment Coatings | 0.3 | 0.3 | 0.3 | 0.3 | 0.3 |
| Non-Volatile Hydrocarbon-Based Oils | 8.5 | 8.5 | 8.5 | 8.5 | 8.5 |
| Phenoxyethanol | 1.4 | 1.4 | 1.4 | 1.4 | 1.4 |
| Other Preservatives | 0.4 | 0.4 | 0.4 | 0.4 | 0.4 |
| Disteardimonium Hectorite | 1.2 | 1.2 | 1.2 | 1.2 | 1.2 |
| Polyol (Glycerin) | 5.0 | 5.0 | 5.0 | 5.0 | 5.0 |
| Other Polyols | 0.6 | 0.6 | 0.6 | 0.6 | 0.6 |
| pH adjusting agents | 0.03 | 0.03 | 0.03 | 0.03 | 0.03 |

TABLE 1-continued (Exemplary and Comparative Formulas)

| Material Name | Ex 1 | Ex 2 | C 1 | C 2 | C 3 |
|---|---|---|---|---|---|
| Extracts | 0.2 | 0.2 | 0.2 | 0.2 | 0.2 |
| Vitamins | 0.2 | 0.2 | 0.2 | 0.2 | 0.2 |

As seen, the compositions shown in Table 1 are generally identical except for the claimed aqueous phase (water is used as the qs material, while the amount and/or specific hydrophilic thickener used varies).

Certain characteristics of the composition were compared, the summary of which is shown in Table 2, below.

TABLE 2

(Summary of Characteristics)

| Characteristic | Ex 1 | Ex 2 | C 1 | C 2 | C 3 |
|---|---|---|---|---|---|
| Texture | Smooth feel, even application. | Smooth feel, even application | Product did not settle well on skin. Streaky application. | Greasy feel. Streaky/draggy application | Tightening feel. Streaky/draggy application |
| Stability | Stable | Stable | Stable | Not stable. Water immediately kicks out, creating white line by the edges. | Not stable. Has white unstable liquid on edges. |

As can be seen, the Exemplary Formulas (Ex 1 and 2), surprisingly, are both stable and have desirable texture characteristics (including streak- and drag-free application), regardless of the amount of thickening agent tested. When the thickening agent was removed entirely (C1), the texture changed, resulting in much less desirable properties. Unexpectedly, other hydrophilic thickening agents did not alleviate the issue—the other agents made the formulas (C2 and C3) unstable and resulted in undesirable textures.

In some embodiments, a method may be provided for applying cosmetics to a face. The method may include applying the cosmetic composition as disclosed herein to the face during a first period of time, and then removing the cosmetic composition from the face during a second period of time after the first period of time.

What is claimed is:

1. A leave-on water-in-oil cosmetic emulsion, comprising:
   an aqueous phase comprising water and a hydrophilic thickening agent consisting of polyvinylpyrrolidone, the aqueous phase being free of other hydrophilic thickening agents;
   a mattifying filler comprising a silicone elastomer;
   an organic ultraviolet filter (UV) consisting of octyl salicylate;
   at least one silicone oil;
   at least one silicone emulsifier; and
   optionally, an inorganic UV filter consisting of UV-grade titanium dioxide.

2. The leave-on water-in-oil cosmetic emulsion according to claim 1, wherein the leave-on water-in-oil cosmetic emulsion is free of silica silylate.

3. The leave-on water-in-oil cosmetic emulsion according to claim 1, wherein the mattifying filler comprises a hectorite.

4. The leave-on water-in-oil cosmetic emulsion according to claim 1, wherein the at least one silicone oil comprises 40-60% by weight of the leave-on water-in-oil cosmetic emulsion.

5. The leave-on water-in-oil cosmetic emulsion according to claim 4, wherein the leave-on water-in-oil cosmetic emulsion includes 10% by weight or less of a hydrocarbon-based oil.

6. The leave-on water-in-oil cosmetic emulsion according to claim 5, further comprising 10% by weight or less of a polyol.

7. The leave-on water-in-oil cosmetic emulsion according to claim 6, further comprising a colorant in an amount of 5-15% by weight of the leave-on water-in-oil cosmetic emulsion.

8. The leave-on water-in-oil cosmetic emulsion according to claim 7, wherein the colorant comprises titanium dioxide in an amount of 5-10% by weight of the leave-on water-in-oil cosmetic emulsion.

9. The leave-on water-in-oil cosmetic emulsion according to claim 7, further comprising a preservative.

10. The leave-on water-in-oil cosmetic emulsion according to claim 9, further comprising a lipophilic thickening agent.

11. The leave-on water-in-oil cosmetic emulsion according to claim 10, wherein the leave-on water-in-oil cosmetic emulsion is substantially free of organic emulsifiers.

12. The leave-on water-in-oil cosmetic emulsion according to claim 11, wherein the leave-on water-in-oil cosmetic emulsion is substantially free of all other materials.

13. The leave-on water-in-oil cosmetic emulsion according to claim 1, wherein the at least one silicone emulsifier is a non-glycerylated silicone.

14. A method for applying cosmetics to a face, comprising:
providing a leave-on water-in-oil cosmetic emulsion according to claim 1;
applying the leave-on water-in-oil cosmetic emulsion to the face at a first point in time; and
removing the leave-on water-in-oil cosmetic emulsion from the face at a second point in time.

* * * * *